United States Patent
Simundic

(10) Patent No.: US 12,318,602 B2
(45) Date of Patent: Jun. 3, 2025

(54) SYSTEM FOR CARDIAC ASSISTANCE, METHOD FOR OPERATING THE SYSTEM AND CARDIAC SUPPORT METHOD

(71) Applicant: Xenios AG, Heilbronn (DE)

(72) Inventor: Ivo Simundic, Wendlingen (DE)

(73) Assignee: Xenios AG, Heilbronn (DE)

( * ) Notice: Subject to any disclaimer, the term of this patent is extended or adjusted under 35 U.S.C. 154(b) by 720 days.

(21) Appl. No.: 17/311,013

(22) PCT Filed: Dec. 5, 2019

(86) PCT No.: PCT/EP2019/083874
§ 371 (c)(1),
(2) Date: Jun. 4, 2021

(87) PCT Pub. No.: WO2020/115234
PCT Pub. Date: Jun. 11, 2020

(65) Prior Publication Data
US 2022/0016410 A1    Jan. 20, 2022

(30) Foreign Application Priority Data

Dec. 6, 2018 (EP) .................................. 18210876

(51) Int. Cl.
*A61M 60/117* (2021.01)
*A61M 60/109* (2021.01)
(Continued)

(52) U.S. Cl.
CPC ........ *A61M 60/851* (2021.01); *A61M 60/109* (2021.01); *A61M 60/117* (2021.01);
(Continued)

(58) Field of Classification Search
CPC .............. A61M 60/851; A61M 60/109; A61M 60/117; A61M 60/216; A61M 60/38;
(Continued)

(56) References Cited

U.S. PATENT DOCUMENTS

| 4,175,264 | A |   | 11/1979 | Schiff |
|-----------|---|---|---------|--------|
| 5,098,370 | A | * | 3/1992  | Rahat ................... A61M 60/531 600/16 |

(Continued)

FOREIGN PATENT DOCUMENTS

| CN | 108367106 A | 8/2018 |
|----|-------------|--------|
| CN | 108601881 A | 9/2018 |
| GB | 2214667     | 9/1989 |

OTHER PUBLICATIONS

Extended European Search Report in European Appln. No. 18210876.1, dated Jun. 17, 2019, 8 pages.

(Continued)

*Primary Examiner* — Catherine M Voorhees
(74) *Attorney, Agent, or Firm* — Fish & Richardson P.C.

(57) ABSTRACT

An extracorporeal cardiac assistance system, comprising a pump being configured to create a fluid flow from a suction line to a pressure line of the system; further comprising a control device configured to control the pump and/or an adjustable flow limiter to provide an adjustable flow rate and/or a pressure, wherein the control device is configured to execute a support mode with a plurality of consecutive support flow rate pulses and/or support pressure pulses interposed on the fluid flow and to execute a weaning mode (Continued)

with a plurality of such pulses, wherein an amount of energy provided to the fluid flow with each pulse is lower in the weaning mode than in the support mode.

22 Claims, 3 Drawing Sheets

(51) Int. Cl.
    *A61M 60/216*     (2021.01)
    *A61M 60/38*     (2021.01)
    *A61M 60/422*     (2021.01)
    *A61M 60/515*     (2021.01)
    *A61M 60/546*     (2021.01)
    *A61M 60/569*     (2021.01)
    *A61M 60/851*     (2021.01)

(52) U.S. Cl.
    CPC .......... *A61M 60/216* (2021.01); *A61M 60/38* (2021.01); *A61M 60/422* (2021.01); *A61M 60/515* (2021.01); *A61M 60/546* (2021.01); *A61M 60/569* (2021.01)

(58) Field of Classification Search
    CPC .............. A61M 60/422; A61M 60/515; A61M 60/546; A61M 60/569
    See application file for complete search history.

(56) References Cited

U.S. PATENT DOCUMENTS

| | | |
|---|---|---|
| 2004/0034272 A1 | 2/2004 | Diaz et al. |
| 2014/0061116 A1* | 3/2014 | Schmitz-Rode .... A61M 60/853 |
| | | 210/321.87 |
| 2015/0030502 A1 | 1/2015 | Gorhan et al. |
| 2016/0000983 A1* | 1/2016 | Mohl .................... A61M 60/17 |
| | | 600/16 |
| 2018/0078159 A1* | 3/2018 | Edelman .............. A61B 5/0215 |
| 2018/0353667 A1* | 12/2018 | Moyer ................ A61M 60/531 |
| 2020/0237987 A1* | 7/2020 | Josephy .............. A61M 60/414 |

OTHER PUBLICATIONS

International Preliminary Report on Patentability in International Appln. No. PCT/EP2019/083874, dated Jun. 17, 2021, 10 pages.
International Search Report and Written Opinion in International Appln. No. PCT/EP2019/083874, Feb. 20, 2020, 13 pages.
Wang et al., "In Vitro Hemodynamic Evaluation of a Novel Pulsatile Extracorporeal Life Support System: Impact of Perfusion Modes and Circuit Component on Energy Loss," Artificial Organs, Jan. 2015, 39(1):59-66, 9 pages.
Hatano Susumu, "Cardiac Recovery During Left Ventricular Assist Device Support," Medical History, Jul. 2017, 262(1):27-32, 8 pages (with English abstract).

* cited by examiner

SYSTEM FOR CARDIAC ASSISTANCE, METHOD FOR OPERATING THE SYSTEM AND CARDIAC SUPPORT METHOD

CROSS-REFERENCE TO RELATED APPLICATIONS

The present application is the national stage entry of International Patent Application No. PCT/EP2019/083874, filed on Dec. 5, 2019, and claims priority to European Application No. EP 18210876.1, filed on Dec. 6, 2018, the disclosures of which are expressly incorporated herein in their entirety by reference thereto

TECHNICAL FIELD

The present disclosure relates to an extracorporeal cardiac assistance system. Furthermore, the present disclosure also relates to a method for operating a cardiac assistance system and to a method for providing cardiac assistance to a patient.

BACKGROUND

US 2015/0030502 A1 discloses an arrangement for extracorporeal life support. This system is suitable for use in interventional cardiology. In particular, this system allows to increase the diastolic pressure of a patient to improve the oxygen balance of the heart muscle. For this purpose, a pump of this system may produce a wave-like surging and subsiding pump output for a pulsatile flow. This pulsatile flow may be provided to the cardiogenic system of a patient to support his heart function and blood flow. Thus, a patient with insufficient heart performance, for example due to a cardiogenic shock, may be treated until the heart has regenerated. The pulsatile support may require the application of a lower amount of inotropes as compared to continuous uniform flow support.

However, issues may arise when the treatment is to be terminated. Here, the patient's heart may have become dependent on the support. Thus, the cardiac system may still not have sufficiently recovered, once the treatment with cardiac support is terminated.

In order to improve the heart's recovery, the heart may be slowly weaned from exogenous cardiac support. For this purpose, the number of pulses may be reduced. For example, a supporting pulse may only be provided with every other heartbeat or every third heartbeat. Such a weaning mode is foreseen by the i-cor Synchronized Cardiac Assist System.

While such a weaning mode may be helpful when envisaging termination of the cardiac assistance, the following is to be considered. By supporting the heart only every other or every third heartbeat, overall mean flow decreases. Once the mean flow drops below a threshold value, a flow mismatch and related alarm may occur. Such circumstances may force the user to revert to the previously applied regular cardiac support. In addition, Wang S. et al. reported ("In Vitro Hemodynamic Evaluation of a Novel Pulsatile Extracorporeal Life Support System: Impact of Perfusion Modes and Circuit Component on Energy Loss.", Artificial Organs 2015, 39(1):59-66) that the pulses under such conditions produce a higher surplus on so-called "hemodynamic energy", which relates to the support dose administered by each pulse. Accordingly, the above-described weaning mode does not appear to be the most preferred option of choice for weaning the heart from exogenous cardiac support. Under some circumstances, the above weaning mode may even generate additional stress for the heart and patient, whenever a heart cycle remains unsupported.

GB 2 214 667 A describes a method to switch from providing the heart function at the "bypass stage" (with the patient's heart activity being stopped) by a heart lung machine to a support mode ("weaning stage") based on counterpulsation. The heart lung machine serves to completely replace the patient's heart function (which is stopped) by the heart lung machine function during the "bypass stage". The "weaning stage" uses counterpulsation to overcome circulation issues when disconnecting the patient from the heart lung machine. In addition, GB 2 214 667 A suggests to implement an "assist mode" (which is another support mode based on catheterization) in order to provide sufficient perfusion—in case the heart-lung machine were incapable to support the patient. U.S. Pat. No. 4,175,264 describes exclusively a support mode for supporting the heart e.g. at every other or every fourth heart beat—without, however, reducing the level of support over time.

SUMMARY

The present disclosure relates to an approach enabling improved weaning from extracorporeal cardiac support.

A first aspect relates to a system for extracorporeal or an implanted intracorporal cardiac assistance. The system may comprise at least one suction line with an internal lumen and at least one pressure line with an internal lumen. Further, the system may comprise at least one pump fluidically connected to the suction line and the pressure line, the pump being configured to pump a fluid, in particular blood, to create a fluid flow from the suction line to the pressure line during use of the system.

Additionally, the system may comprise a control device configured to control the pump and/or an adjustable flow limiter to provide an adjustable flow rate and/or a pressure of the fluid flow in the pressure line. Additionally or alternatively, an adjustable flow rate and/or a pressure of the fluid flow may also be provided in the suction line. The system may be specifically used for treatment of cardiogenic shock and cardiac arrest of any origin, in particular for post-emergency treatment for increasing long-time survival rates. The system may also be used for circulatory support during e.g. interventional cath lab procedures. The system may be configured as a wearable cardiac assistance device, in particular a wearable ventricular assistance device, enabling non-stationary treatment.

The control device may be configured to execute a support mode with a plurality of consecutive support flow rate pulses and/or support pressure pulses applied on the fluid flow, in particular essentially synchronized to a heart cycle of the heart supported by the system in use or essentially synchronized to the heart beat of a patient. The control device may additionally be configured to execute a weaning mode with a plurality of consecutive weaning flow rate pulses and/or weaning pressure pulses applied on the fluid flow, in particular essentially synchronized to a heart cycle of the heart supported by the system in use, wherein an amount of energy, in particular kinetic energy, provided to the fluid flow with each pulse is lower in the weaning mode than in the support mode. Preferably, a weaning pulse may be provided to every heartbeat of the patient or e.g. to every other heart cycle.

Due to the weaning mode with pulses having less energy than the pulses of the regular support mode, optimized cardiac support may be ensured, even when weaning the patient from the cardiac support. The energy of the weaning pulses may be adjusted to the level of mean flow so that no or at least less surplus hemodynamic energy (SHE) is produced and/or delivered to the patient. Surplus hemodynamic energy may also relate to energy equivalent pressure. SHE may be defined as the integral of fluid flow rate (in 1/min) multiplied by the pressure (in mmHg) over time divided by the integral of the fluid flow rate (in 1/min), preferably over the duration of one single pulse. SHE can also be considered as the dose for supporting and/or assisting a cardiovascular system and/or the heart.

By applying the weaning mode described above, the heart suffers less from reduced cardi-ac support. While the system for cardiac assistance is hence switched or alternated between a support mode and a weaning mode, cardiac support may still be provided at the same frequency of the support mode, e.g. at every or every other heartbeat. Yet, the extent of support is advantageously adapted, such that the patient may gradually accommodate over time to a reduced cardiac assistance. Accordingly, the patient does not suffer from an otherwise instantaneous loss of support or from an instantaneous change in assistance frequency, e.g. when suddenly providing assistance at every second heartbeat only (instead of every heartbeat). Thereby, aspects the present disclosure allow the combination of two distinct modes, i.e. a support mode and a weaning mode. Thus, the present disclosure provides a system which is configured to carry out two distinct modes simultaneously, in parallel or in an alternating manner. Under such circumstances, the heart is thereby not required to compensate for overly supportive exogenous pulses on the one hand and for lack of any supportive pulse for the following heart cycle on the other hand. Instead, a homogenous quasi-continuous support may be ensured when applying the weaning mode that gently reduces the cardiac support as a function of time. In particular, sufficient supply with oxygen may be ensured for every heartbeat even when weaning the patient from the cardiac support. The nature of the weaning mode applied by the device is considered specifically beneficial when weaning from support after cardiopulmonary bypass surgery or whatever cardiac intervention, such as heart transplant or a coronary artery bypass graft intervention, wherein the cardiac activity may be essentially replaced by e.g. a heart-lung machine.

"Cardiac assistance" is thus typically not understood as an assistance in the course of a heart intervention when the heart function is stopped (i.e. does typically not refer to the complete replacement of the heart function by a heart lung machine). Rather, it may be understood as supporting the blood pumping function of the patient's heart. In other words, such support is provided in addition to any spontaneous activity of the patient's own cardiac system, such that, instead of fully replacing a patient's own cardiac activity so (as a heart lung machine does during heart surgery), the patient's intrinsic cardiac performance is artificially modified and enhanced. The pump is preferably a non-occlusive blood pump, such as a diagonal pump, that is beneficial by preventing damage to blood cells, such as red blood cells. The respective control algorithm of the control device may be individually chosen for the support mode or the weaning mode.

The suction/pressure lines may each comprise a cannula. In particular, the suction line may comprise a venous cannula and the pressure line may comprise an arterial cannula. At least one of the lines may be configured for being introducable into a heart, in particular a human heart, especially the left ventricle, which is also designated as the "aortic ventricle". The fluid flow may flow through the internal lumen of each line. The pump may be fluidically connected to the internal lumina of the lines so that the fluid flows from the suction line to the pressure line through the pump. The suction line may also additionally be connected to a fluid reservoir, in particular to a blood reservoir, for example with a dedicated branch. Such an approach may allow treatment of a bleeding patient while simultaneously providing a blood transfusion and/or maintaining sufficient blood volume in the cardiac system of the patient. Both lines may comprise entrance and exit passages for sucking a fluid into the lumina and subsequently discharging the fluid from the internal lumen, in particular blood from and into a bloodstream of a patient, respectively. The lines may be disposables and/or exchangeably connected to the system, in particular the pump. Thereby, hygienic standards are met when using the system for the treatment of more than one single patient. Alternatively or additionally, the cannulae may be disposables and/or exchangeably connected to the system.

The pumping operation may result in decreasing pressure in the suction line and increasing pressure in the pressure line, while generating a fluid flow from the low pressure side to the high pressure side. The pump is preferably designed not to damage the blood or blood cells, for example by heat and/or mechanically. The pump may comprise a moving pumping part, such as a propeller, in particular an impeller, and a motor. The movement of the pumping part and/or the actuation provided by the motor, in particular rounds or revolutions per minute of the motor and/or propeller, may be controlled by the control device.

The pulses in each mode may be emitted successively, i.e. one after the other, e.g. quasi-continuous, but as discrete and/or consecutive pulses. There may be a lag period or downtime period whenever the mode is changed. Preferably, the mode is only changed within so the period between two pulses. The control device will thus not prematurely terminate a pulse by initiating a mode change, but only foresee any mode change prior to eliciting the next pulse supplying another energy level. Pulses may be provided consecutively until the mode is changed and/or system is deactivated.

Preferably, the pulses are synchronized to the physiological operation mode of the patient's heart, in particular his heart rate. For example, one or more than one pulse may be applied per heart cycle. Synchronization may also additionally or alternatively relate to the physiological operation mode of the different heart ventricles and/or generally measurements of an electrocardiograph. Such synchronization may be particularly useful for a system, which comprises several pressure and/or suction lines, which are located at different sites of the cardiovascular system of the patient, in particular the ventricles, of the patient's heart. Preferably, the pulses may be synchronized to the R wave, also called "R spike", recorded by an ECG, which may be taken as an indicator of the time of blood ejection by the heart. For advanced cardiac assistance, the pulses are preferably generated such that they essentially arrive at the exit of the pressure line when the aortic valve of the patient is closed. For that purpose, the control device may be configured to implement latency in the system; in particular pump and lines and respective fluid transport time, in particular when the timing of the pulses is based on the R wave.

The pulsatile pressure in the system may be a pressure wave running along the fluid flow path, in particular also passing through the cardiac system of the patient, once the cardiac assistance system has been operationally connected to this patient. Pulsatile flow rate in the system may be a flow wave passing along the fluid flow path, in particular also passing through the cardiac system of the patient, once the cardiac assistance system has been operationally connected to the patient. The pressure wave and flow wave may be coupled, in particular, they may be phase shifted due to a change in pump speed and/or flow limiter setting. A phase shift of the pressure pulse and flow rate pulses may establish increased blood flow whenever needed by the patient. Independently, however, a phase shift increases pressure at the cardiac system whenever the delivery of the pulses exerts less stress, for example when the aortic ventricle is closed. An undesired reflux is thus avoided, once the pressure line is connected to a ventricle of the patient. Accordingly, the pressure line may preferably be connected to the left ventricle or to the aorta guiding blood from the left ventricle to the patient's circulatory system, while the suction line is preferably connected to the right ventricle or to a vein supplying blood to the right ventricle.

One or more flow limiter(s) may be foreseen at whatever location of either of the lines or within the pump. Or, a flow limiter may be realized within any other part fluidically connecting the system for allowing the fluid flow to pass therethrough.

The additional energy resulting from each pulse may preferably be applied to the fluid in the pressure line, thus increasing flow rate and/or pressure at the pressure line. The energy may be applied to the fluid when sucking the fluid from the suction line. Thereby, a decrease in pressure at the suction line and/or an increase in flow rate at the suction line may typically occur. This decrease of pressure and increase in flow at the suction line may also be beneficial for supporting the patient's cardiac function, depending on the placement of the suction line, e.g. to reduce the afterload at the left ventricle portion of the heart.

The modes to be applied may be chosen and/or changed, for example by the use of an input device as a component of the system. An example of such an input device may be a touchscreen or button. The input device may also define a set of parameters for each mode, such as mean flow in each mode and/or SHE for pulses according to whatever mode. The parameter set may also allow to further define the character of the pulse, such as the duration, shape, absolute and/or relative maximum and/or average flow rate change and/or pressure pulse of the pulses in whatever mode, in particular independent of or in relation to the setting defined for another mode. This may allow to deliver pulses having a higher degree of similarity to the pulses of the heart cycle, thereby allowing to reduce additional stress to the patient's heart. Preferably, the mean flow is adjusted to the patient's individual level of cardiac assistance for each operation mode. Alternatively or additionally, the control device may determine an appropriate mean flow in the weaning mode based on the required mean flow in the support mode. Thus, weaning is carried out using reduced (e.g. minimized) strain and/or improved (e.g. optimized) cardiac support.

In a preferred embodiment, the system is configured to provide a base fluid flow. In particular, the control device is configured to adjust the base fluid flow. The base flow may ensure basic support for the cardiac system, thus ensuring sufficient blood flow in the patient and sufficient oxygen supply to its tissue as a default support. Further, the base flow may prevent clotting of the blood in the system. As a further benefit, provision of a base flow may reduce latency when delivering the pulses. The base fluid flow in the weaning so and the support mode may be identical or the base fluid flow in the weaning mode (weaning base flow) is different from the base fluid flow in the support mode (support base flow). Thereby, a reduced weaning base flow (as compared to support base flow) may be established to improve the weaning process, e.g. thus shortening the weaning process period, such that the heart reverts within a shorter period of time to its physiological (unsupported) state.

The system may comprise more than one pump. In particular, a first pump may be used to supply the base fluid flow and a second pump to generate the pulses. The first pump may exhibit an increased half-life for its continuous operation, thus reducing maintenance efforts. The second pump may be characterized by a shorter reaction time and thus be especially suitable for pulse delivery. Individual characteristics of the pumps according to the system's needs may thus establish a less expensive and more reliable system than by using one single pump complying with all individual requirements. Two pumps may also ensure ongoing operation of the system by establishing a level of redundancy, due to the provision of e.g. two pumps, such that at least one functional pump is left to enable both base flow and pulse generation in case of dysfunction of another pump. In analogy, the control device may be configured to control the first pump to ensure base flow and the second pump to deliver pulses.

The base fluid flow may comprise a base flow rate and/or base pressure supplied to a patient under cardiac assistance operation. The base flow rate and/or base pressure may be zero. Preferably, the base flow rate and base pressure is set to predetermined values greater than zero, in particular each or at least one of them is set to a predetermined value depending on a parameter representing the patient's physiological (unsupported) cardiac heart function, in particular a measured and/or determined parameter of the patient's heart. The values may be automatically set by the input device and/or by a caregiver. The base flow rate and/or base pressure may be continuously zero and/or greater than zero and may be invariant over time, with the pulses applied on the continuous base fluid flow support. The base flow rate may be defined by a base operation of the pump and/or a base setting of the flow limiter and may thus be adjusted by the flow limiter and/or pump settings.

For example, the system may be configured to provide a base flow between 0.2 l/min up to 1.5 l/min. The maximum mean weaning flow may be 0.5 l/min to 2.5 l/min. The mean flow may be calculated by considering or disregarding flow peaks resulting from the pulses. Preferably, the mean flow is calculated based on the base flow and the additional flow resulting from the pulses.

In a preferred embodiment, the system, in particular the control device, is configured to generate the flow rate pulses and/or pressure pulses by increasing the pump's output, in particular the pump speed, when generating the pulse over the base pump performance. Adjusting the pump, for example by adjusting voltage and/or current provided to its motor, is an efficient and reliable option for generating the pulses. Another exemplary option to adjust the pump output is to adjust the position and/or effective angle of blades and/or vanes of the pump. For example, increase in pump output (for exerting a pressure pulse) is typically reduced when applying the weaning mode as compared to the support mode. Since the pulse energy may be predetermined, increased pump output is typically also pre-determined and/or may be modified by the user or caregiver. For example, a user or caregiver may adjust pulse duration, which is correspondingly effected by an increased pump output. For generating a pulse, the pump or rather its component, e.g. an impeller, is typically accelerated (e.g. rpm of the pump are increased up to higher values, e.g. up to a maximum) for a period shorter than the pulse duration. The peak speed may thereafter be reduced to the base speed for reverting to the base fluid flow characteristics, or to 0, which is preferred when applying e.g. a two pump system. The pump's increased output may also be actively stopped by an actuator, e.g. a brake or applying inverse voltage characteristics. Such measures may e.g. allow to align the wave form of the pulse to more closely resemble the wave form of the patient's physiological (unsupported) heart pulses.

In a preferred embodiment, the system, in particular the control device, is configured for adjusting the pump output for generating the weaning flow rate pulses and/or weaning pressure pulses and for generating the support flow rate pulses and/or support pressure pulses. The weaning flow rate or pressure pulses is/are characterized by a smaller pulse amplitude and/or smaller pulse width. As a result, the weaning pulse introduces less energy to the cardiac system of the patient than the support pulse without requiring a structural re-design of the pulsatile cardiac assistance system. Less energy for pulses applied by the weaning mode may imply a reduced period of increased pump output (e.g. resulting in shorter pulse duration) and/or performance reduced amplitude of the pump (e.g. reduced increase in rpm of the pump thus relating in lower peak rpm values) during a pulse in comparison to the pulse settings in the support mode. Pump output may be dependent on propeller acceleration; e.g. the propeller does not exhibit peak rpm (smaller amplitude) and/or does not exhibit peak rpm for an extended period (smaller pulse width) for pulses during the weaning mode as compared to the support mode. Preferably, both pulse duration (pulse width) and peak speed (pulse amplitude) of the pump are smaller for weaning pulses than for support mode pulses. Pump speed of the pumping unit may be controlled by the voltage and/or current applied to an electrical pump.

In a preferred embodiment, the system, in particular the control device, is configured to generate the flow rate pulses and/or pressure pulses by adjusting the flow limiter differentially and/or employ the flow limiter for delivery of shorter pulses, when defining the weaning flow rate pulses and/or weaning pressure pulses as compared to the support flow rate pulses and/or weaning pressure pulses. A flow limiter, such as a valve or a lumen with an adaptable cross-section, may be used. Further, the flow limiter may react faster than the pump to an external signal, since the flow limiter does not require the pump's components to be accelerated. The system, in particular the control device, may thus be configured to generate the flow rate pulses and/or pressure pulses by adjusting the flow limiter according to a predetermined value for a predetermined time period compared to a base flow limiter setting and/or support mode flow limiter setting. Such an embodiment may not require a pump or a flow limiter may be used in combination with a pump.

The system may thus also be configured to adjust the nature of the pulses both by the flow limiter and the pump. Under such circumstances, the wave form of the pulses may be modulated and adapted according to the patient's need. Further, such a set-up may easily allow to independently control pressure pulses and the flow rate. Additionally, the flow limiter and the pump may act in combination to establish a redundant system. In particular, the system may be based on one single base flow pump only, as the flow limiter may replace the pulse pump or at least the pulse pump. The output of the base flow pump may thus be increased appropriately.

In a preferred embodiment, the system, in particular the control device, is configured to adjust the flow limiter for reduced through flow rate and/or to modulate, in particular extend, the period of lower (reduced) through flow by the flow limiter generating the weaning flow rate pulses and/or weaning pressure pulses as compared to the support flow rate pulses and/or support pressure pulses. Preferably, the pulse may be delivered by the pump without modifying the pump's output in combination with the flow limiter, which generates the pulse and/or reduces energy consumption when applying the weaning mode.

In a preferred embodiment, the system, in particular the control device, is configured to increase the pump speed by 2000 to 5000 revolutions per minute (rpm/min), preferably by 3000 rpm/min to 4500, alternatively or additionally by 3500 rpm/min to 6000 rpm/min, preferably 4500 rpm/min, in case of acute cardiac arrest, when generating the support flow rate pulses and/or support pressure pulses. That technical property may enable the system to treat a larger variety of pathological heart conditions, in particular any type of heart insufficiency.

In a preferred embodiment, the system, in particular the control device, is alternatively or additionally configured to generate support flow rate pulses and/or support pressure pulses having a pulse duration of about 150 ms (milliseconds) to 250 ms, preferably of about 200 ms.

Pulse duration (pulse width) may be defined as duration of accelerated and/or increased speed of the pump, increased flow rate and/or pressure as compared to base flow or the period zero or initial values before onset of the pulse. Pulse duration is typically composed of phases of increasing and decreasing portions of pressure pulses and/or flow rate pulses. The systolic portion of pulse typically relates to an increase in pump speed and/or pressure, in particular relative to the base flow. The systolic portion of the pulse may comprise about 5% to 70% of the total pulse duration, preferably 5% to 30%, more preferably about 5-15%, e.g. 10%. In contrast, the diastolic portion typically relates to a decrease in pump speed and/or pressure, usually after the pulse peak has been reached. The diastolic portion is typically achieved by decreasing the pump's speed, active braking and/or pump coasting. The diastolic portion of the pulse may comprise about 95% to 30% of a total pulse duration, preferably 95% to 70%, more preferably 85-95%, e.g. about 90%. Thereby, pressure and fluid flow rate pulses are generated that more closely resemble the physiological (unsupported) heart pulses.

The system may be configured to detect a cardiac arrest of the patient, for example by a heart pulse measurement and/or by an electrocardiograph. The system may increase cardiac support, in particular energy charge of the pulses, whenever a cardiac arrest is detected. Upon detection, a pre-set increased value is automatically applied to support the patient until emergency medical treatment becomes available. The negative effects of a temporary cardiac arrest may thus be combatted. Additionally or alternatively, the system may include an alarm function when detecting cardiac arrest. Thus, the control device is configured to execute an automatic or manually triggered emergency cardiac arrest operation mode. The control device can automatically switch from either the support or the weaning mode to such an emergency mode. Preferably, the control device is configured to automatically switch to the support mode after cardiac arrest to ensure the required cardiac support.

In a preferred embodiment, the system, in particular the control device, is configured to increase a pump speed by 100 to 4000 revolutions per minute (rpm/min), preferably by 500 to 3499 rpm/min, for generating weaning flow rate pulses and/or weaning pressure pulses. In a preferred embodiment, the system, in particular the control device, is alternatively or additionally configured to deliver weaning flow rate pulses and/or weaning pressure pulses with a pulse duration of 50 ms to 250 ms, preferably 75 ms to 200 ms. By selecting such values, the requirements for sufficient cardiac support on the one hand and for a shorter weaning period on the other hand may be reconciled such that the level of cardiac support may be reduced over time allowing the patient's physiological heart function to fully regenerate within a shorter period of time than by applying prior art technologies.

In a preferred embodiment, the system, in particular the control device, is configured to provide flow rate pulses and/or the pressure pulses in the form of rectangular pulses or in wave form, in particular by essentially sinusoidal waves. A sinusoidal pulse exerts less strain on the cardiac system of the patient, since instant pressure and flow rate changes are avoided. Further, such pulse shapes can reliably be reproduced for a larger series of pulses, which may allow the patient's heart to better adapt to the applied cardiac support function. Also, sinusoidal pulses essentially emulate physiological cardiac pressure and flow rate waves. Pump performance for a predetermined period may thus establish a wave-like character as a function of time.

In a preferred embodiment, the system, in particular the control device, is configured to enable a mean flow in the weaning mode that is equal to or smaller than the mean flow foreseen for the support mode. Additionally or alternatively, the system, in particular the control device, may be configured to establish a base flow in the weaning mode that is equal to or smaller than the mean flow provided in the support mode. A reduced mean flow and/or base flow may assist to achieve regeneration and/or weaning of the patient's heart from cardiac support in an expedited manner. The system may also comprise a warming device that determines whether the mean flow provided by the system has dropped below a threshold level. The warning device may deliver a warning signal, such as an optical or acoustic alarm signal. The threshold level may be varied and may typically be set to a lower value for the weaning mode than for the support mode. Individual thresholds for the weaning and the support mode are preferred.

In a preferred embodiment, the system comprises at least one sensor configured to measure one or more cardiac values to determine the heart rate and heart rhythm of the patient and/or comprises an interface configured for connection with a cardiac sensor for measuring one or more cardiac parameter(s) of the patient, in particular an electrocardiograph. The system, in particular the control device, is configured to adjust cardiac support depending on the measured cardiac timing (heart rate, heart rhythm, timing of the heart cycle phases) and/or measured cardiac parameters. In particular, such an adjustment to the measured signals may affect the onset of pulse generation. Synchronization of pulse generation and the patient's heart cycle is thus enabled. In addition, such a measurement may also be used to determine the patient's cardiac performance and/or monitor his cardiac status and/or health status. In particular, a cardiac arrest may be detected by the monitoring of such a sensor as well. For example, the system may be configured to synchronize pulse generation and the cardiac cycle's R wave of the patient's cardiogram. It may be further foreseen to trigger pulses such that the system's latency does not result in a delay of the cardiac support or weaning pulses, but enables a simultaneous and convergent onset of the support/weaning pulse and the patient's physiological pulse phase. The weaning or support pulse timing may be dependent on the heart valve action and/or heart muscle contraction. The electrocardiograph may be implanted or arranged extracorporeally. The electrocardiograph may be used to determine the systolic point of pressure which may be used as indicator for activating increasing or accelerating the pump's output.

In a preferred embodiment of the system, the at least one sensor is configured to measure at least one of the following cardiac signals: a mean arterial pressure, systolic pressure, diastolic pressure, cardiac output, ejection fraction, heart rate, heartbeat, inotrope level, catecholamine level/dosing, and determination of the heart cycle wave, in particular the R-wave. The measurement of the heartbeat may comprise start, duration and/or strength of the heart muscle function for individual heart cycles or for a sequence of heart cycles.

One or more of these signals may allow to synchronize pulse generation with the physiological heart operation mode of the patient. Alternatively, some signals may not be measured individually, but may be derived or calculated from other measured signals.

In a preferred embodiment of the system, the control device is configured to reduce the amount of energy by each weaning pulse until at least one of the measured cardiac values falls below or goes beyond a (predetermined) threshold level during execution of the support mode. This may allow the system to automatically determine whether at all and to what extent cardiac support is needed for the patient. That function may assist supporting the patient's heart to the lowest possible extent, preferably including a safety margin. Such a system may also be used for initial or continuous analysis of the level of cardiac support required. Such a test may be applied when initially executing the weaning mode or at pre-determined intervals during the cardiac support period. The cardiac support level determined as sufficient, e.g. pulse energy level, may be pre-set by the control device as the required minimum pulse energy level, in particular for the weaning mode. The thresholds defining insufficient cardiac function are typically individually defined for the at least one cardiac parameter. During the test, the energy level may be reduced continuously or stepwise. Preferably, energy reduction is carried out discontinuously, as a multitude of pulses, e.g. at least 5 or 10 pulses, of a given energy level are to be applied for allowing the cardiac system to adapt to the modified support level. If the reduced energy level results in medically acceptable cardiac signals, the pulse energy may be further reduced for the cardiac system to adapt again to lower pulse energy.

In a preferred embodiment of the system, the control device is configured to adjust the flow rate pulses and/or the pressure pulses, in particular their energy and/or duration. That adjustment may be derived from measured signals of the cardiac cycle. Also the system or the control device may be configured to synchronize generation of the flow rate pulses and/or the pressure pulses to a heartbeat of the patient based on the measured cardiac signals. Pulse generation and heartbeat may, for example, be synchronized such that pulse initiation is directly linked to the onset of the heart cycle (as measured, for example, by ECG). Alternatively or additionally, an anticipating control function may be implemented in the control device. The control device may be configured to anticipate the next heartbeat by recording and analyzing a series of preceding heartbeats. Depending on the observations recorded for various pulses previously measured, the character and the onset of the next pulse is calculated prior to that heartbeat.

In a preferred embodiment of the system, the control device is configured to deliver a weaning pulse above a predetermined energy threshold and/or to generate a mean weaning flow (rate) going beyond a predetermined flow (rate) threshold. The system is thus configured for a cardiac support preventing one or more of the measured cardiac signals (e.g. representing cardiac performance) to fall below or to go beyond a predetermined threshold defined individually for each measured parameter/signal. Such thresholds may counteract insufficient cardiac support when operating in the weaning mode. In particular, the system may be configured to automatically reduce the level of cardiac support, unless measured cardiac signals fall below or go beyond such thresholds. Thereby, any risk of low level cardiac support is minimized and the patient's safety is reliably maintained. Alternatively or additionally, the system may be configured to provide a warning signal, whenever any of the cardiac signals falls below or exceeds the predetermined threshold. The appropriate threshold may be a threshold hardwired into the system or may be defined by a user or a caregiver. For allowing the warning signal to be perceived, the system may comprise an output device, such as a display, touchscreen and/or a loudspeaker. Alternatively or additionally, the system may be linked to a mobile phone presenting an alarm function for the user and/or to a remote medical centre. Thresholds may be applied when using the system in the support mode. The control device may be configured for allowing to individually set the thresholds.

In a preferred embodiment of the system, the control device is configured to execute the weaning mode by continuously modifying the energy level of the weaning mode. The weaning mode may thus comprise a first weaning mode operation mode with a plurality of first weaning flow rate pulse and/or of first weaning pressure pulses and a second weaning mode with a plurality of second weaning flow rate pulses and/or second weaning pressure pulses. The energy level of each pulse of the second weaning mode is lower than the energy level of the pulses of the first weaning mode; with a third, fourth etc. series of weaning mode pulses following, each exhibiting a lower pulse energy level than the preceding weaning mode pulse series. Such a weaning mode allows to progressively wean the patient from cardiac support. It may reduce cardiac support quasi-continuously. For example, the pulse energy level may be reduced by incremental steps, such as 0.001% or less, preferably 0.00001% or less for each pulse or each pulse series, e.g. of at least 5 or 10 pulses, as compared to the previous (higher) value. Progressive weaning thus may be an option, which only marginally compromises the patient's cardiac system and reduces cardiac support by discrete steps of minor or minimum pulse energy reduction.

The onset of a pulse or the increase of the pulse energy level may be set and/or adapted as described above. The following pulse may be separated from the previous pulse by a dead period or by in-between pulses, in particular by several ramping pulses for a gradual adjustment of the energy provided by the first and the second weaning pulse. The progressive weaning mode may comprise plurality of first and second weaning pulses. The first pulse or the first series of pulses (of the same energy level) may be automatically replaced by the second pulse or the second series of pulses (of the same energy level, but providing less cardiac support than the first weaning mode series of pulses) or may be set by manual control, in particular using the input device of the system, such as a button or touchscreen.

In a preferred embodiment of the system, the control device is configured to execute the first weaning mode for a predetermined time period and to thereafter automatically execute the second weaning mode, the third weaning mode etc., each e.g. for a pre-set period of time. The control device may include a timer function for this purpose. The timer function may be alternatively actuated by manual input or may be actuated by the control device based on cardiac support information of the system itself (e.g. energy level of the pulses) and/or based on the analysis of cardiac signals.

The control device may thus be configured to automatically switch from the support mode to the weaning mode after predetermined support mode time period. Weaning is considered as essential to counteract the heart's permanent dependency on exogenous cardiac energy supply, thereby rendering the cardiac system addicted to exogenous cardiac support. The control device may also be configured to switch to the second weaning mode with lower cardiac support after a predetermined time period and/or to automatically terminate support, e.g. to shutdown the system. Alternatively or additionally, a warning signal may be sent out, in case of failure or detected cardiac dysfunction, in particular in case of emergency conditions.

In a preferred embodiment of the system, the control device is configured to execute the first weaning mode until one or more of the measured cardiac signals have reached the predetermined threshold value. Thereafter, the second weaning mode phase (applying less cardiac support) is automatically executed. Such a regimen may be continued by a third, fourth etc. weaning mode phase. The system may allow to automatically reduce cardiac so assistance, once the heart has recovered sufficiently at given cardiac support level. The control device may be configured to reduce the pulse energy provided, e.g. to define a $\Delta E$ for the first and second weaning mode phase depending on measured cardiac signals and/or determined stroke volume. The control device may also increase the cardiac support in response to insufficient cardiac performance as a result of applying reduced cardiac support in the second weaning mode phase. Thus, the weaning mode may be further automatically refined in order to well meet the patient's cardiac support needs. Such a system control may also be defined as an automatic weaning adjustment mode in response to the patient's needs. Thus, the adjustment may react in real-time to the patient's heart conditions. Termination of support and/or shut-off of the system may controlled based on the above principles as well.

In a preferred embodiment, the system comprises an oxygenator configured to enrich the fluid flow with oxygen. Such an oxygen delivery module is provided for further cardiac support. Heart tissue may regenerate upon increased oxygen supply. The control device to may be configured to control the oxygen delivery module and to adjust the oxygen delivery by measuring the fluid's partial oxygen gas pressure supplied to the fluid flow. The partial oxygen gas pressure may vary depending on the executed support or weaning mode and/or the applied pulse energy.

A second aspect relates to a method for operating a cardiac assistance system, in particular a system as described by the first aspect. Accordingly, the first aspect completely reads on the second aspect, and vice-versa.

The method may comprise pumping a fluid, in particular blood, to create a fluid flow from a suction line to a pressure line, in particular by means of at least one pump. The at least one pump, optionally in combination with an adjustable flow limiter, may be controlled to adjust the flow rate and/or the pressure of the fluid flow in the pressure line according to the executed mode of the system, in particular by a control device. The support mode operates by a sequence of consecutive support flow rate pulses and/or support pressure pulses, which are applied to the patient's cardiac system, in particular essentially synchronized to the physiological heart cycle of the patient's heart. Pulse delivery is controlled by the control device. Further, a weaning mode characterized by a sequence of consecutive weaning flow rate pulses and/or the weaning pressure pulses is applied to the fluid flow, in particular essentially synchronized (by the control device) to the patient's heart cycle. The so pulse energy level in the weaning mode is lower than the pulse energy level in the support mode. Accordingly, the patient is subject to cardiac support by using an improved weaning technology, thereby re-establishing the heart's physiological stroke volume.

During operation of the cardiac assistance system, a fluid flow is generated from and through the suction line, to and through a pressure line, in particular through internal lumina of the lines. The fluid flow passes through the pump. Pulses may be preferably applied on the flowing fluid or, less preferably, any flow of the fluid may be triggered by the application of pulses only, while absence of pulses brings the flow to a standstill. Accordingly, the resulting fluid flow may be continuous or discrete as a function of time. Either the support mode and/or the weaning mode may be executed according to the method. The method may also comprise switching between the modes (e.g. any of the modes described above). Typically, only one mode (e.g. only the weaning mode or only the support mode) is executed at a given moment in time.

In a preferred embodiment of the method according to the second aspect, the support mode is executed initially and the weaning mode is executed thereafter. The method thus initially applies the support mode to support the cardiac function, e.g. following cardiogenic shock or cardiac arrest. Once the heart function, e.g. the stroke volume has reached physiological levels as a result of the cardiac support by the support mode, the method allows to continuously wean the patient and its heart from the support mode in order to allow the heart itself to recover in the best way possible.

In a preferred embodiment of the method, a base fluid flow is established by the system, in particular with the control device adjusting the base fluid flow. The base flow may be adjusted to a predetermined setting or according to a support level set by a caregiver.

In a preferred embodiment of the method, the flow rate pulses and/or pressure pulses are generated by increasing pump performance, in particular pump speed, for establishing an extended pulse duration (pulse width) and/or enhanced pulse amplitude in comparison to a base pump performance. In a preferred embodiment of the method, pump performance for generating weaning flow rate pulses and/or weaning pressure pulses is increased less or for a shorter pulse period than for the support flow rate pulses and/or support pressure pulses.

In a preferred embodiment of the method, the flow rate pulses and/or pressure pulses are so generated by adjusting the flow limiter differentially. Thus, the flow limiter is adjusted for restricting the pulse period of the weaning flow rate pulses and/or of weaning pressure pulses in comparison to the support flow rate pulses and/or support pressure pulses. In a preferred embodiment of the method, the flow limiter is adjusted to reduce the flow rate. It may be adjusted to be applied for an extended period of time when applying the weaning flow rate pulses and/or weaning pressure pulses as compared to the support flow rate pulses and/or support pressure pulses.

In a preferred embodiment of the method, pump speed may be increased by 2000 to 5000 revolutions per minute (rpm/min), preferably by 3000 rpm/min to 4500, more preferably by 3500 rpm/min and/or 4500 rpm/min, e.g. in case of an acute cardiac arrest for the support flow rate pulses and/or support pressure pulses. The support flow rate pulses and/or support pressure pulses may exhibit a pulse duration of about 150 ms (milliseconds) to 250 ms, preferably about 200 ms.

In a preferred embodiment of the method, pump speed may be increased by 100 to 4000 revolutions per minute (rpm/min), preferably by 500 to 3499 rpm/min for the weaning flow rate pulses and/or weaning pressure pulses. The weaning flow rate pulses and/or weaning pressure pulses may exhibit a pulse duration of 50 ms to 250 ms, preferably 75 MS to 200 ms.

In a preferred embodiment of the method, the flow rate pulses and/or the pressure pulses are provided in the form of a wave, in particular an essentially sinusoidal wave.

In a preferred embodiment of the method, a mean flow rate (for the weaning mode) is provided to be equal to or smaller than a mean flow rate provided by the system in the support mode. The mean flow rate may be adjusted by the user or predetermined. Pulses may be adjusted accordingly, in particular in accordance with the mean flow rate defined. Accordingly, the level of support of the weaning mode and the energy of the weaning pulses may be selected based on other settings, e.g. base flow rate and/or base pressure.

In a preferred embodiment of the method, cardiac performance and/or the heart's pulse cycle is determined, in particular based on one or more measured cardiac signals, which may, for example, be derivable from electrocardiography. Cardiac support is adjusted such so that the patient's cardiac performance reaches a physiological level and/or in accordance with the patient's cardiac cycle.

In a preferred embodiment of the method, the measured cardiac signal is at least one of mean arterial pressure, systolic pressure, diastolic pressure, cardiac output, ejection fraction, heart rate, heartbeat, inotrope level, catecholamine dose or blood level, and/or one or more other (electrical) signals typically measured by electrocardiography, such as an R-wave.

In a preferred embodiment of the method, the energy level applied on the fluid flow by each weaning pulse is reduced, unless one or more of the measured cardiac signals are recorded, which indicate cardiac insufficiency or other pathological events, in particular significantly deviate from a value measured or defined at the onset of the execution of the weaning mode and/or fall below or go beyond a predetermined threshold value.

In a preferred embodiment of the method, the flow rate pulses and/or the pressure pulses, in particular their energy and/or duration, may be adjusted depending on the measured cardiac signals or on the determined cardiac performance (e.g. stroke volume). They may also be adjusted to synchronize the flow rate pulses and/or the pressure pulses to the patient's heart cycle based on the measured signals (e.g. ECG signals).

In a preferred embodiment of the method, the pulse energy level applied on the fluid flow by each weaning pulse may be set to exceed a predetermined energy threshold. A mean weaning flow rate should exceed a predetermined flow rate threshold. It may also be adjusted for one or more of the measured cardiac signals to represent physiological values, e.g. to maintain a predetermined cardiac performance beyond a lower threshold level.

In a preferred embodiment of the method, the weaning mode is executed as a progressive weaning mode. During execution of the weaning mode at least a plurality of first weaning flow rate pulses and/or a first weaning pressure pulses is initially executed. A subsequent plurality of second weaning flow rate pulses and/or a second weaning pressure pulses is executed thereafter. The second pulse energy level applied on the fluid flow is lower than for the first weaning mode pulses, unless cardiac signals indicate that the control device is required to revert to the energy level of the higher output first weaning pulse mode.

In a preferred embodiment of the method, the first weaning mode is executed for a predetermined time period and then the second weaning mode is automatically executed afterwards. In another preferred embodiment of the method, the first weaning mode is executed until one or more values of the measured cardiac signals improve, in particular go beyond or fall below a pre-determined threshold level indicating recovered cardiac function after execution of the first weaning mode. The second weaning mode is automatically executed thereafter.

In a preferred embodiment of the method, the fluid flow is enriched by oxygen, in particular by means of an oxygenator (oxygen delivery module) of the system. The fluid's oxygen partial gas pressure may be measured together with cardiac signals, in particular by the control device. Upon improvement of the heart function and/or its recovery, the oxygen supply may be reduced so as to also wean the cardiac system from exogenous oxygen supply.

A third aspect relates to a method for providing cardiac assistance to a patient. The method of the third aspect may use a system according to the first aspect, which may be operated according to the second aspect. Accordingly, the first and second aspect may constitute features, benefits and preferred embodiments of the third aspect, and vice-versa.

The method may comprise pumping a fluid, wherein the fluid is blood of the patient or a blood-like substitute fluid being compatible with the cardiac system of the patient, such as an artificial blood substitute, to create a fluid flow from a suction line to a pressure line, in particular by means of at least one pump. The suction line may be connected to a blood vessel of the patient, in particular a vein, a heart chamber or a ventricle of the patient's heart, e.g. by a catheter and the pressure line is connected to another blood vessel of the patient, in particular an artery, another heart chamber or another ventricle of the patient's heart, e.g. by a catheter. The pump and/or an adjustable flow limiter may be controlled to adjust a flow rate and/or a pressure of the fluid flow in the pressure line according to a currently executed mode of cardiac assistance, in particular by a control device. There may be provided a support mode with a plurality of consecutive support flow rate pulses and/or support pressure pulses applied on the fluid flow, in particular essentially synchronized to the heart cycle of the heart of the patient, in particular provided by the control device. A weaning mode with a plurality of consecutive weaning flow rate pulses and/or weaning so pressure pulses may be applied on the fluid flow as well, in particular essentially synchronized to the heart cycle of the patient, in particular provided by the control device. The pulse energy level applied on the fluid flow is typically lower in the weaning mode than in the support mode.

In analogy to the second aspect, either support mode or weaning mode may be executed as a feature of the method. The method may also comprise alternating support/weaning modes. Usually, only one of the modes is executed at a given moment in time. Preferably, the support mode is executed during treatment of one specific patient. Upon recovery of the patient's heart due to the assistance by the support mode, the weaning mode is applied.

Herein, "blood vessel" refers to arteries and veins. They are, however, also understood to comprise heart cavities as well, in particular heart ventricles or chambers. The method may allow blood to be transported, in particular pumped, from one blood vessel to another blood vessel with an increase in flow rate and/or pressure, optionally with a support pulse or weaning pulse applied thereon. The method may allow cardiac support of a patient suffering from a heart event, e.g. a cardiogenic shock or cardiac arrest or whatever type of heart insufficiency. The method as a method of treatment may allow the patient and its cardiac system to be slowly weaned from cardiac support. Thus, any loss of heart function due cardiac support addiction is avoided.

Further features result from the claims, the exemplary embodiment and the drawings. The features and combinations of features mentioned above in the description as well as the features and combinations of features mentioned in the exemplary embodiment below can be used not only in the combinations indicated but also in other combinations without leaving the scope of the invention.

DETAILED DESCRIPTION

Figure 1:
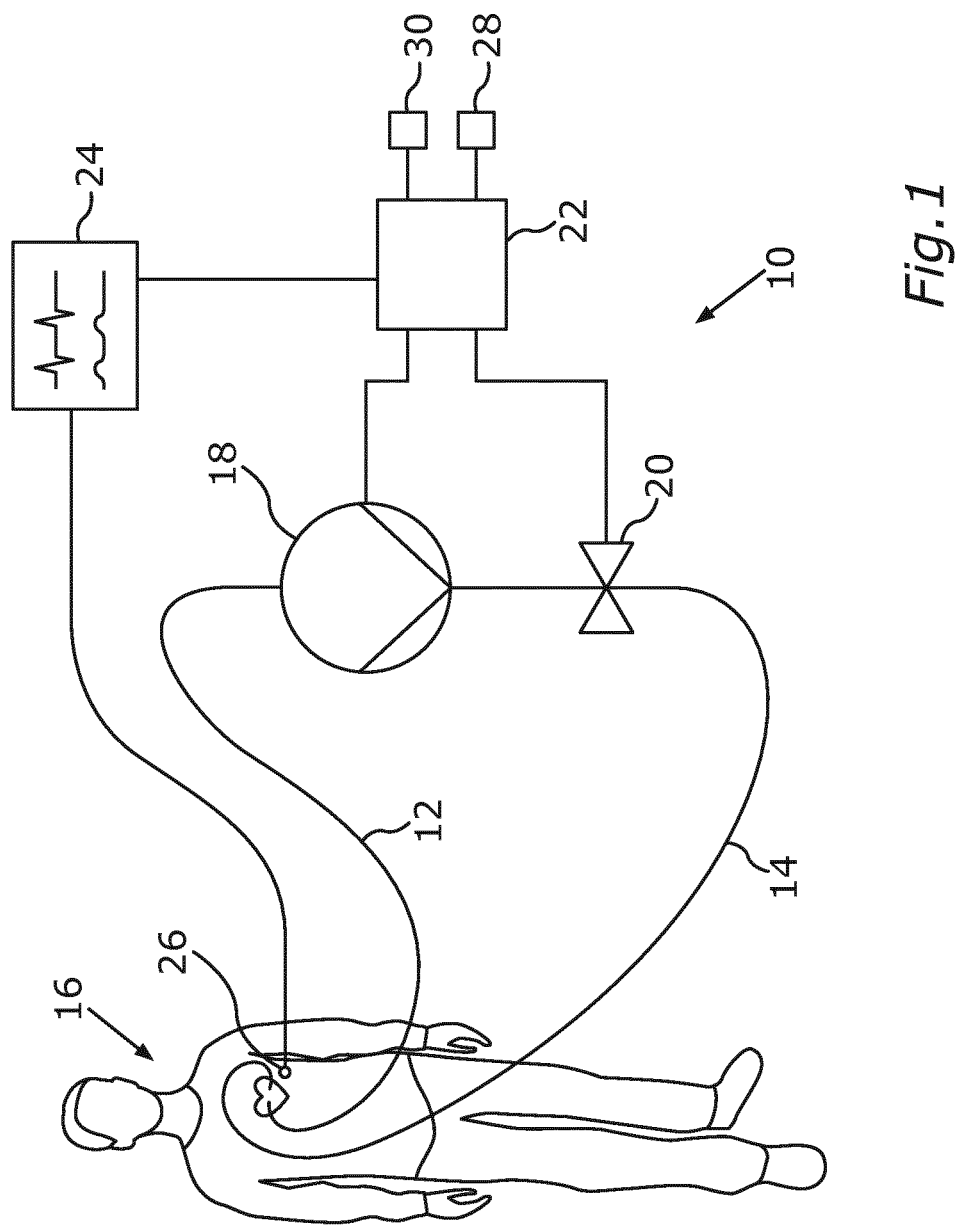
FIG. 1 shows a schematic illustration of a system for cardiac assistance.

FIG. 1 illustrates in a schematic view a system 10 for cardiac assistance. The system 10 comprises a suction line 12 with an internal lumen and a pressure line 14 with an internal lumen. As can be seen from FIG. 1, the system is connected to a patient 16, in particular with the suction line 12 being connected to vein or the right ventricle of the heart and the pressure line 14 being connected to the left ventricle of the patient 16, e.g. positioned closely to the aortic valve of the heart. The ends of the lines 12, 14, e.g. by using catheters, allow blood to pass from the patient 16 to the internal lumens and vice-versa when connected to the patient 16.

The system 10 comprises a pump 18 that is fluidly connected to the suction line 12 and the pressure line 14. The pump 18 is configured to pump blood so as to create a fluid flow essentially from the right ventricle of the heart to the suction line 12, passing the pump 18 and flowing via the pressure line 14 back to the heart of the patient 16, in particular to the aortic ventricle of the patient 16. That circuit may also be designated as fluid flow path. To control the fluid flow through the flow path, the system 10 may—in addition to the pump 18—also further comprise an adjustable flow limiter 20, which is a valve in the present example. The valve 20 is also located in the fluid path, meaning that the blood flow also passes through the flow limiter 20. Accordingly, both the pump 18 and the flow limiter 20 may be used in combination to provide an adjustable flow rate and an adjustable pressure of the fluid flow, in particular blood in the present example, through or in the pressure line 14.

For that purpose, the system 10 comprises a control device 22 that is configured to control the pump 18 and the flow limiter 20 in order to adjust the flow rate and the pressure. For example, the control device 22 may control pump speed, pressure increase by the pumping action and/or pumped volume of blood, and/or may also adjust the position of the flow limiter 20, e.g. the degree to which the valve is opened or closed.

Furthermore, the system 10 comprises an electrocardiograph 24 that is functionally connected to the control device 22. For example, the electrocardiograph 24 may transmit signals to the control device 22 which correspond to signals measured by the electrocardiograph 24. The signals may be, for example, electric signals transmitted by an electric connection cable, or radio-waves transmitted wirelessly. This allows the control device 22 to control the pump 18 and the adjustable flow limiter 20 based on measured and/or estimated cardiac signals recorded by the electrocardiograph 24. To measure cardiac signals of the patient 16, the electrocardiograph 24 comprises one or more sensors 26, which are attached or adhere to the patient's skin in the present example.

Furthermore, the system 10 also comprises an input device 28, such as a keyboard or a touch screen. The input device 28 is configured to allow adjustment the settings of the system, in particular of the control device 22. This allows a caregiver, a user or the patient 16 to adjust the cardiac assistance provided by the system 10, which may also be called the level of cardiac assistance, the level of cardiac support and/or the cardiac support.

In addition, the system 10 also comprises an output device 30. The output device 30 may be configured to display the settings of the system 10, for example allowing a caregiver to check the level of cardiac assistance provided at a given moment and/or to send out warning signals in case of dysfunction or medical emergency. The output device 30 may comprise, for example, a display and/or a loudspeaker, or may be comprised within the input device 28, in particular when configured as a touchscreen.

The control device 22 may be configured as a computer or a circuit board, for example. The control device 22 may comprise a permanent or non-permanent memory device and may be configured to execute computer executable code, which may be a control algorithm for system 10. The control device 22 may be electrically connected to other parts of the system 10, in particular the electrocardiograph 24, the output device 30, the input device 28, the pump 18 and/or the valve 20. The control device 22 may also instead be connected wirelessly to any of the above-mentioned components. Furthermore, the system 10 may be configured as a wearable ventricular assistance device, so that mobile cardiac assistance may be enabled for the patient 16. The system 10 may comprise a power supply, such as a rechargeable battery. Some or all or the components of system 10 may be redundantly provided, so that cardiac assistance may even be ensured in case of technical dysfunction or failure of one of the components, such as a damaged motor of the pump 18. When configured as a wearable device, the system 10 may include a casing so and/or may comprise means to attach the system 10 to the patient 16. In the case of wearable device, the electrocardiograph 24 may be replaced by another sensor device for measuring cardiac signals of the patient 16.

The pump 18 is preferably a non-occlusive blood pump, such as a diagonal pump. The flow limiter 20 may be configured as a valve exhibiting a fast reaction time, for example with an electrically and/or magnetically movable plate for restricting the diameter of the flow path along a given portion of the path.

The control device 22 is configured to execute a weaning mode with a plurality of consecutive weaning flow rate pulses with and/or weaning pressure pulses applied on the fluid flow, wherein the pulses are essentially synchronized to the heart cycle of the patient 16 supported by the system 10. Synchronisation is performed based on the cardiac signals recorded by the electrocardiograph 24, for example synchronized with the onset of the R-wave of the heart of the patient 16. The R-wave may allow to precisely predict closure of the aortic valve of the patient 16, thus being a cardiac signal usable for controlling synchronization of the pulses and the heart cycle of the patient 16. Furthermore, the control device 22 is also configured to execute a support mode with a plurality of consecutive support flow rate pulses and support pressure pulses applied on the fluid flow. Again, those pulses are also essentially synchronized to the heart cycle of the patient who is supported by the system in use. Synchronization of the pulses with the heart cycle of the patient 16 may be adopted for the weaning pulses and support pulses in the very same way. For example, pulse onset and/or pulse arrival at the end of the pressure line 14 may be identically established for both support mode and weaning mode.

With the support mode, the system 10 may provide cardiac assistance for a patient 16 suffering from e.g. a cardiogenic shock. Due to the cardiogenic shock, the heart muscle of the patient 16 is typically damaged and thus be incapable of ejecting a blood volume output per heartbeat which is sufficient for supplying oxygen to the periphery of the patient 16. Also, the heart of the patient 16 itself suffers from lack of oxygen support. Without exogenous support by the cardiac assistance system 10, the patient's heart may therefore further lose contractility due to e.g. heart muscle atrophy. The survival rate of patients compromised due to progressive heart insufficiency may thus be lowered.

By providing the cardiac support with the system 10 in the support mode, physiological blood flow characteristics and oxygen supply in the periphery and for the heart of the patient 16 is ensured. To further improve the supply of oxygen, the system 10 may also comprise an oxygenator that is configured to enrich the blood pumped from the suction line 12 to the pressure line 14 with additional oxygen increasing the blood's partial oxygen gas pressure.

Upon support by the cardiac assistance system 10, the heart may have recovered such that cardiac assistance may be terminated. However, abrupt termination was found to stress the patient 16's circulation, in particular his heart, and should therefore be avoided. Also, the heart was found to become addicted to cardiac assistance. Without cardiac support, the heart thus fails, even though recovered to eject sufficient stroke volume under cardiac support.

In order to adjust the patient 16's heart to conditions without cardiac assistance, the system 10 is configured to execute the weaning mode. Generally, the weaning mode is intended to supply less cardiac assistance to the patient 16 than the support mode. In the prior art, weaning may be established by providing a pressure pulse and flow rate pulse synchronized only to every other or every third heartbeat. However, such a weaning mode was found to undersupply the patient's heart of the unsupported intermitted heartbeats and oversupply the heart at the supported heartbeats. The level of cardiac assistance provided with each pulse may also be called as cardiac energy, in particular hemodynamic energy (HE). Oversupplying cardiac assistance for every second heartbeat and insufficient cardiac assistance in-between the supported heartbeats may overall be detrimental to the heart of the patient 16 and should therefore be avoided. A level of support is defined as surplus hemodynamic energy (SHE).

For establishing improved weaning, the system 10 and in particular the control device 22 is configured to execute a weaning mode. The pulse energy provided to the fluid flow with each pulse is lower in the weaning mode than in the support mode. This may allow the system 10 to ensure cardiac assistance for every heartbeat of the patient 16 while reducing overall cardiac assistance when operating at the weaning mode. For example, the level of support and thus pulse energy in the weaning mode can be set by the input device 28 and be adapted to the patient 16's heart function or whatever conditions.

The level of support given may also be determined based on cardiac signals measured by so the electrocardiograph 24. In the weaning mode, the energy level as set in and provided by the support mode may be considered as the baseline for the provision of cardiac support. That baseline level is reduced for the pulses provided by the system 10 in the weaning mode. This may allow to support each heartbeat of the patient 16 with a synchronized weaning pulse while still reducing overall cardiac support. Preferably, the system 10 synchronizes both in the support mode and the weaning mode a pulse to every heartbeat of the patient. Due to reduced pulse energy in the weaning mode, the heart can slowly be adapted to regain cardiac performance (e.g. stroke volume per heartbeat) without exogenous support. Furthermore, recovery of the heart muscle tissue may be expedited, since the heart is trained for enhanced cardiac performance by itself as compared to applying the support mode only. The method may thus support the recovery process and/or shorten cardiac assistance treatment.

Energy levels of the weaning mode and/or switching from the support mode to the weaning mode may be controlled based on the lapse of a predetermined time of executing the support mode and/or based on the cardiac values measured by the electrocardiograph 24. Adjustment of the energy level of the weaning mode and/or switching from the support mode to the weaning mode may be executed automatically by the control device 22. For example, the system 10 can be configured to automatically switch to the weaning mode, once the patient 16 has received cardiac assistance in the support mode for a predetermined period of time and/or for a predetermined number of heartbeats. The predetermined signal of time period can be set by the input device 28. Furthermore, the measured cardiac signals may be used to determine the overall patient's health status and/or heart performance. Depending on his health status and/or heart performance, the control device 22 may be configured to automatically switch to the weaning mode and/or reduce the energy of each pulse in the weaning mode so as to adjust the level of a cardiac assistance. Hereby, the weaning period is shortened. In addition, recovery of the heart tissue is found to be successfully established.

The control device 22 may also be configured to perform a test of the status of the cardiac system of the patient 16. For example, the control device 22 may reduce the energy level of the pulses in the weaning mode, until one or more of the measured cardiac signals of the patient 16 is/are altered by a predetermined absolute value or by a relative percentage based on an initial value recorded prior to the onset of the pulse energy level reduction. The system 10 may thus to automatically adjust the pulse energy level in the weaning so mode. Accordingly, the system 10 is capable to progressively wean the patient 16 from the cardiac assistance according to the patient's individual cardiac performance. Such an approach is found to improve the recovery of the patient 16's compromised heart.

Any setting of the control device 22 or other settings of the system 10, in particular any setting based on the above-described automatic adjustment of the energy level may be displayed in the output device 30 so that the current status of the system 10 may be checked.

Figure 2:
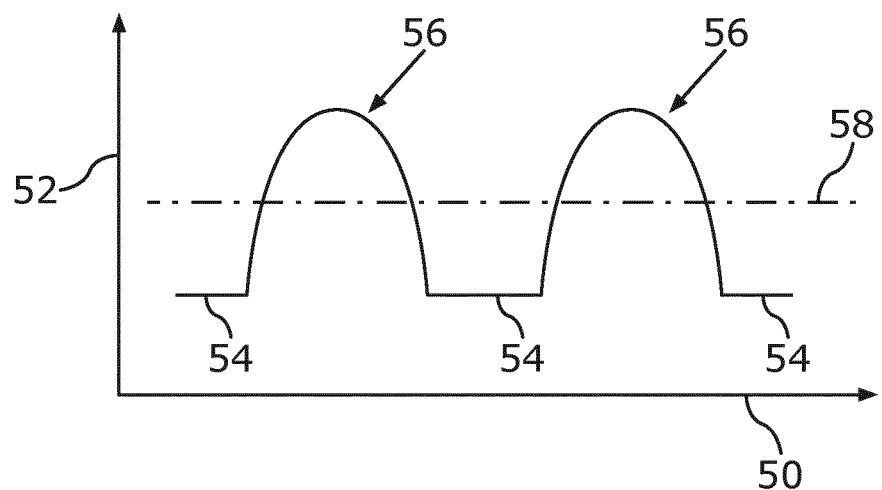
FIG. 2 illustrates, in a diagram, settings for synchronized cardiac assistance with the system according to FIG. 1.

FIG. 2 illustrates in a diagram the fluid flow of system 10, e.g. for approximately two pulses according to the support mode. In FIG. 2, the axis 50 represents "time (ms)" and the axis 52 represents "flow" (litres per minute). As indicated by the horizontal parts 54 of the graph shown in FIG. 2, the system 10 enables a base flow for overall cardiac assistance, also avoiding blood clotting, in particular in the lumina of the lines 12, 14 and/or the pump 18, and may also increase a reaction time of the system 10. Furthermore, applied on the base flow, the system 10 generates pulses 56, two of which are illustrated in FIG. 2. The pulses 56 have a symmetric (single partial) sinusoidal shape. The pulses 56 may reflect an increase in the revolutions per minute of the pump 18, for example by 3500 rpm/m. Increase of revolutions of the pump 18 for a pulse may be adjusted such that pulses of the desired pulse energy are generated. Increase in the number of revolutions per time unit (for a given pulse 56) of the pump 18 is lower for the weaning mode than for the support mode. Accordingly, support for the flow rate is lower for the weaning mode. The peak of a given pulse typically reflects the maximum performance of the pump 18. Thereafter, the pump's performance is reduced to the level prior to the pulse generation and thus to the support required for the base flow.

In the shown examples, pulses 56 have a pulse duration that determines the level of energy applied on the fluid flow. The pump's 18 enhance performance for an extended period of time (with respect to its base flow performance) increases the energy of pulse 56. For example, in the shown example, the pump 18 is accelerated for about 200 ms in the support mode. By comparison, in the weaning mode, the pump 18's performance may only be increased for less than 200 ms, e.g. from about 75 ms to 200 ms for a given pulse, resulting in a weaning pulse with shorter length. In addition or alternatively, also the pump 18's peak performance (pulse amplitude) may be reduced compared to the support mode. Accordingly, pulse energy and cardiac assistance are reduced in the weaning mode so compared to the support mode.

As is also illustrated by line 58 in FIG. 2, the overall mean flow rate is higher than the base flow provided by the system 10 due to the additional pulses applied thereon. The mean flow rate may also be considered as a parameter indicating the overall cardiac assistance applied. For example, a maximum weaning flow rate may be chosen to be 2.5 litres per minute and a minimum weaning flow rate may be 1.5 litres per minute. By comparison, the base flow rate may be set to about 0.2 litres per minute to up to 1.5 litres per minute. Although the mean flow rate is reduced for the weaning mode, additional oxygen (more than establishing the mean flow rate) is still supplied to the tissue on the patient 16.

Figure 3:
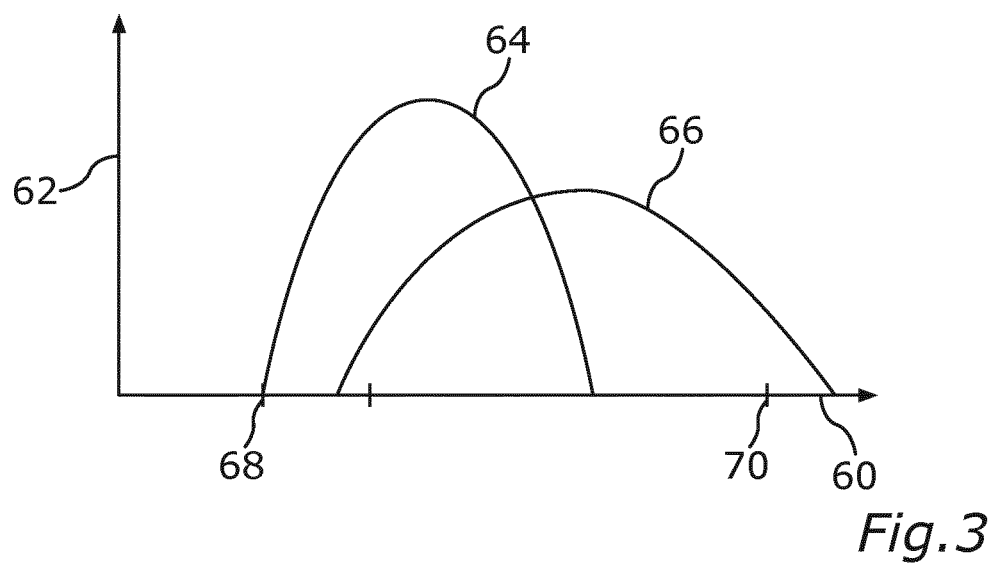
FIG. 3 illustrates in a diagram a flow rate pulse and a pressure pulse interposed on a so fluid flow by the system according to FIG. 1.

FIG. 3 illustrates in detail an exemplary pulse provided to the cardiac assistance of the patient 16 by the system 10. The graph with axis 60 (time) and axis 62 (pressure in mmHg or flow rate in litres per minute) depicts curves 64, 66. Curve 64 illustrates the pressure pulse generated by the system 10. Curve 66 illustrates the flow rate pulse generated by the system 10. The flow rate pulse is phase-shifted to the pressure pulse, thus following the pressure pulse. The system 10 initially increases the pressure which results in an increase of flow rate. However, by the flow limiter 20, the relative shift of pressure pulse and flow rate pulse may be adjusted. In particular, pressure pulse and flow rate may be decoupled from each other.

Preferably, the pressure pulse and/or flow rate pulse arrive(s) at the left aortic ventricle of the patient's 16 heart at the moment of aortic valve closure or shortly thereafter. That approach allows to support the physiological heartbeat pulse of the patient 16 himself Undesired reflux through the aortic valve is essentially counteracted. For that purpose, the control device 22 may synchronize the pulse generation to a recorded R-wave of the patient 16, also considering latency of the system 10. Latency may occur, as e.g. the pump 18 exhibits a lag period until acceleration starts. Also, the fluid arrives via the pressure line 14 at the heart of the patient 16 with delay, which may be required to be considered for synchronization.

FIG. 3 illustrates how to measure the surplus hemodynamic energy. The surplus hemodynamic energy is an integral over the flow rate multiplied by the pressure over pulse duration divided by an integral of the flow rate of the pulse duration (see below formula with q'≙flow rate, p≙pressure and t≙pulse duration). The duration of the flow pulse is defined as the onset of pressure increase beyond base pressure, as indicated by reference numeral 68. The end point of the pulse may correspond to the flow rate reaching a threshold value corresponding to the base flow rate (reference numeral 70).

$$SHE[\text{mmHg}] = \frac{\int q' * p\, dt}{\int q'\, dt}$$

Figure 4:
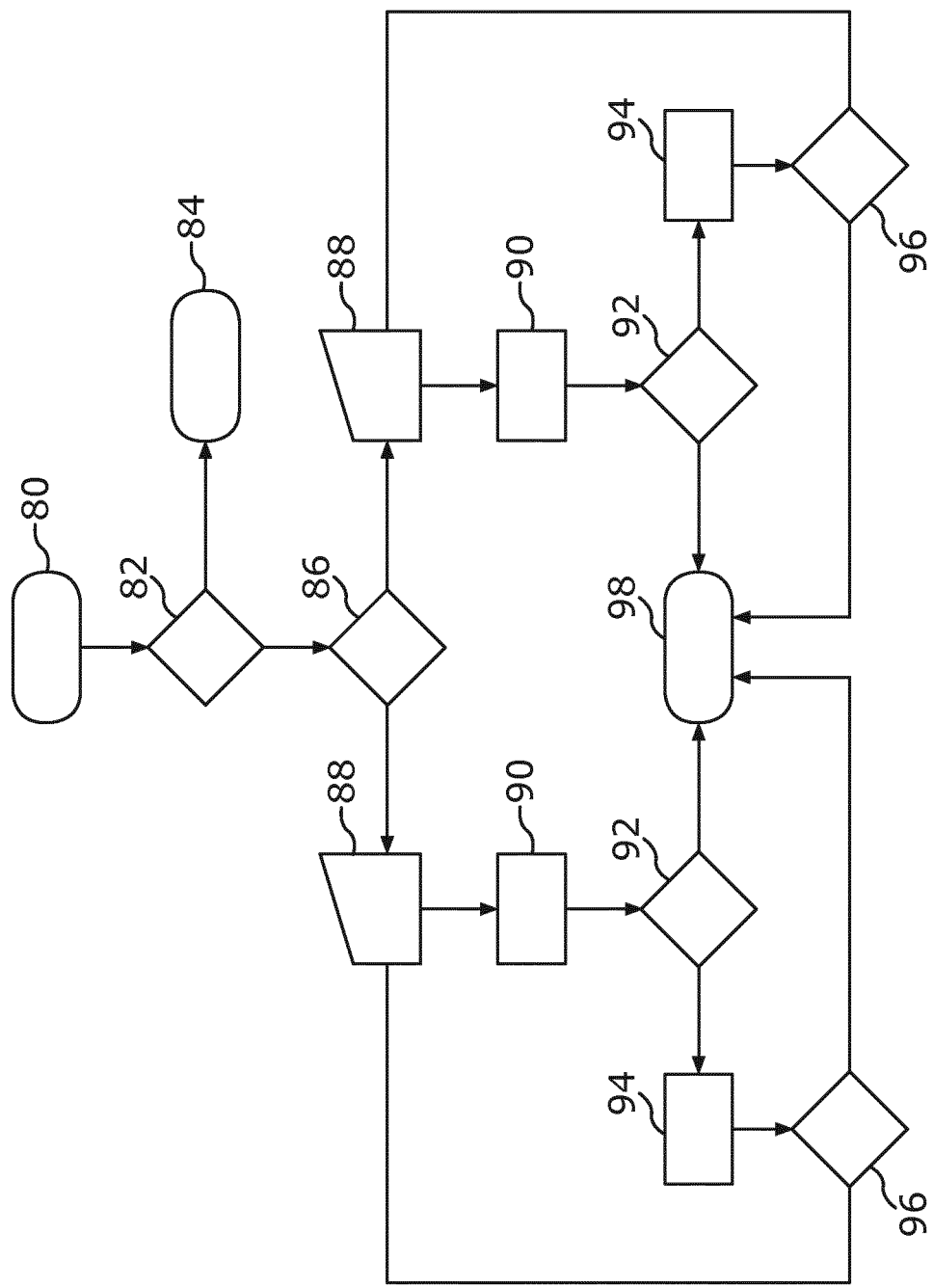
FIG. 4 illustrates in a flow diagram a control algorithm for the system according to FIG. 1.

FIG. 4 illustrates in a flow diagram a control method that may be executed by the control device 22 to operate the system 10. Box 80 denotes the first step of the control method, which may correspond to the onset of the cardiac assistance of the patient 16 by the system 10. In box 82, it is determined whether the patient 16 requires pulses of the support mode or the weaning mode. Determination may be based on measured cardiac signals or be set manually, for example by a caregiver. If patient 16 requires the support mode for cardiac assistance, the control algorithm continues by executing the support mode, as illustrated by box 84. Otherwise, the control algorithm continues with the determination of cardiac support required for the weaning mode, as illustrated by box 86. The required level of cardiac assistance during weaning may be selected, for example by selecting a higher level and a lower level of cardiac assistance. Alternatively or additionally, the level of cardiac support in the weaning mode may also be determined based on measured cardiac signals.

In the example given in FIG. 4, the control device is able to provide two levels of cardiac support in the weaning mode, while more than two levels are possible. The control method executes the same program with the target energy level being distinct for the alternative weaning pulses. However, the control device may be configured to modify its mode so as to allow automatic switching between the two (or more) levels of cardiac assistance foreseen in the weaning mode, for example based on measured cardiac signals and/or determined cardiac performance (not shown). Only one side of the control algorithm following decision box 86 is described. It is understood that the other side is distinct in terms of the pulse energy level only.

Upon passing decision box 86, the method induces flow reduction, as illustrated by box 88. Flow reduction 88 is achieved by an adjustment of the increase of pump performance (e.g. rounds per minute of the pump 18) for a pulse relating to the base performance of the so pump 18, as illustrated by box 90. Afterwards, it is determined according to decision box 92 whether reduction matches with the required pulse energy level. For example, matching may be established by comparing the provided mean flow rate with a target mean flow rate. Using the mean flow rate for controlling the energy level of the weaning mode is advantageous, as the mean flow rate is readily measured. Such a feedback loop may also allow to compensate for individual conditions, such as viscosity of the blood of the patient 16, kinks and bends in the lines 12, 14 and/or loss of performance by the pump 18 due to continued use. For example, the mean flow rate may be measured by a flow sensor in one of the lines 12, 14 of the system 10.

Decision box 90 may also additionally or alternatively effect a change in pulse duration in order to reduce the energy level. It may be determined in decision box 92 whether reduction in pulse duration matches with the required pulse energy level. Measuring mean flow rate for controlling the energy level of the weaning flow may also be beneficial, since it allows for simultaneous analysis or adjustment of both pulse duration and peak performance of the pump 18 and their impact on the energy level without requiring separate measurements and their aggregation.

If the actual mean flow rate does not match the target mean flow rate in decision box 92, the method continues with further reduction of the pump 18 performance and/or of pulse duration (period of increased performance of pump 18). The method may be designed to either reduce pump performance and/or pulse duration individually and consequently or jointly until the target value is met. In the example illustrated in FIG. 4, preferably only the performance of pump 18 (number of revolutions per minutes) is changed in step 90. Pulse duration is only changed in step 94, in case the target flow rate is not achieved by a (reduced) pump speed alone for pulse generation in step 90. Thereafter, it is determined in decision box 96 whether the target value is realized by the weaning pulses or whether further reduction is required.

If according to decision box 96 further reduction is required, a further reduction loop is envisaged as illustrated by box 88, executing the steps reiteratively. Otherwise, control method continues by executing the weaning mode in box 98 with the appropriate settings for pump performance increase (pulse amplitude) and/or pulse duration (pulse length).

REFERENCE NUMBER LIST

10 system
12 suction line
14 pressure line
16 patient
18 pump
20 flow limiter
22 control device
24 electrocardiograph
26 sensors
28 input device
30 output device 50 axis
52 axis
54 horizontal parts
56 pulse
58 line
60 axis
62 axis
64 pressure curve
66 flow rate curve
68 numeral
70 numeral
80 box
82 box
84 box
86 box
88 flow reduction
90 box
92 box
94 step
96 box
98 box

The invention claimed is:

1. A system for extracorporeal cardiac assistance, comprising:
   at least one suction line having an internal lumen;
   at least one pressure line having an internal lumen;
   at least one pump fluidly connected to the suction line and the pressure line, the pump being configured to pump blood to enable blood flow from the suction line to the pressure line;
   a valve;
   a control device configured to control at least one of the pump and the valve to adjust a flow rate of the blood in the pressure line,
   wherein the control device is configured to execute a support mode in which at least one of the pump and the valve applies pressure pulses to the blood,
   wherein the control device is configured to execute a weaning mode in which at least one of the pump and the valve applies pressure pulses to the blood,
   wherein pressure applied on the blood by the pressure pulses of the weaning mode is lower than pressure applied on the blood by the pressure pulses of the support mode,
   wherein the pressure pulses, in both the support mode and the weaning mode, are synchronized with a heartbeat of a patient, and
   wherein the system is configured for connection with a cardiac sensor for measuring one or more cardiac values of the patient, and wherein the control device is configured to reduce an amount of energy provided to the blood flow by each weaning pulse until at least one of the one or more measured cardiac values falls below or goes beyond a predetermined threshold value.

2. The system according to claim 1, wherein the system is configured to implement a base blood flow.

3. The system according to claim 2, wherein the control device is configured to generate the pressure pulses as a function of an output of the pump.

4. The system according to claim 3, wherein the control device is configured to modulate pulse amplitude and/or pulse width by contracting pump output.

5. The system according to claim 3, wherein the control device is configured to generate the pressure pulses by adjusting the valve differentially thereby modulating pulse width and/or pulse amplitude.

6. The system according to claim 3, wherein the control device is configured to adjust the valve to reduce the blood flow and/or to decrease the size of the valve for a longer duration.

7. The system according to claim 1, wherein the system comprises:
   at least one cardiac sensor configured to measure a cardiac timing of the patient,
   wherein the control device is configured to adjust cardiac support in response to measured cardiac output and/or in response to measured cardiac parameters.

8. The system according to claim 7, wherein the control device is configured to adjust the pressure pulses, in response to the measured cardiac output and/or the measured cardiac parameters.

9. The system according to claim 7, wherein
   the control device is configured to control at least one of the pump and the valve to provide pressure on the blood by each weaning pulse to be above a predetermined threshold, and/or
   the system is configured to provide cardiac support to prevent one or more of the values of a cardiac performance to deteriorate beyond a predetermined cardiac performance threshold.

10. The system according to claim 1, wherein the control device is configured to execute the weaning mode as a progressive weaning mode, wherein the weaning mode comprises a first weaning mode portion comprising a sequence of first weaning pressure pulses and a subsequent second weaning mode portion comprising a sequence of second weaning pressure pulses,
    wherein pressure applied on the blood by a pulse is lower in the second weaning mode portion than in the first weaning mode portion.

11. The system according to claim 10, wherein the control device is configured to:
    execute the first weaning mode portion for a predetermined time period and/or until one or more values of measured cardiac signals improve, and
    automatically execute the second weaning mode portion thereafter.

12. The system according to claim 1, wherein the system comprises an oxygenator.

13. The system according to claim 1, wherein the support mode comprises a sequence of consecutive support pressure pulses applied on the blood flow.

14. The system according to claim 7, wherein the control device is configured to control at least one of the pump and the valve to generate a mean weaning flow above a predetermined flow threshold.

15. A method for operating a cardiac assistance system, comprising:
    extracorporeally pumping blood to create a blood flow from a suction line to a pressure line by operating at least one pump,
    operating the at least one pump, using a control device, to adjust a flow rate of the blood in the pressure line according to a currently executed mode of the system,
    measuring one or more cardiac values of a patient with a connection to a cardiac sensor;
    wherein the control device operates the at least one pump in a support mode to generate a plurality of consecutive support pressure pulses interposed on the blood flow, synchronized to a heartbeat of a heart supported by the system in use,
    wherein the control device operates the at least one pump in a weaning mode to generate a plurality of consecutive weaning pressure pulses interposed on the blood flow, synchronized to the heartbeat of the heart supported by the system in use, wherein pressure applied on the blood by the pressure pulses in the weaning mode is lower than pressure applied on the blood by the pressure pulses in the support mode, and wherein the control device is configured to reduce an amount of energy provided to the blood flow by each weaning pulse until at least one of the one or more measured cardiac values falls below or goes beyond a predetermined threshold value.

16. The method according to claim 15, wherein the support mode is executed and then the weaning mode is executed.

17. The method according to claim 16, wherein the weaning mode is a progressive weaning mode, wherein the weaning mode comprises a first weaning mode portion comprising a sequence of first weaning pressure pulses and a subsequent second weaning mode portion comprising a sequence of second weaning pressure pulses.

18. The method according to claim 17, wherein pressure applied on the blood by a pulse is lower in the second weaning mode portion than in the first weaning mode portion.

19. The method according to claim 15, wherein the control device is configured to adjust a valve to reduce the blood flow and/or to decrease the size of the valve for a longer duration.

20. The method according to claim 15, wherein the control device is configured to modulate pulse amplitude and/or pulse width by contracting pump output.

21. The method according to claim 15, wherein the method comprises measuring a cardiac timing of a patient with at least one cardiac sensor.

22. The system according to claim 1, wherein the control device is configured to alternate between the support mode and the weaning mode.

* * * * *